United States Patent
Ward

(10) Patent No.: US 9,757,211 B2
(45) Date of Patent: Sep. 12, 2017

(54) STENTS FOR PLACEMENT OF ORTHODONTIC ATTACHMENTS, AND METHODS OF PRODUCING AND USING SUCH STENTS

(71) Applicant: Robert Ward, Winnipeg (CA)

(72) Inventor: Robert Ward, Winnipeg (CA)

( * ) Notice: Subject to any disclaimer, the term of this patent is extended or adjusted under 35 U.S.C. 154(b) by 0 days.

(21) Appl. No.: 15/238,243

(22) Filed: Aug. 16, 2016

(65) Prior Publication Data

US 2017/0105816 A1   Apr. 20, 2017

Related U.S. Application Data

(60) Provisional application No. 62/299,634, filed on Feb. 25, 2016, provisional application No. 62/243,837, filed on Oct. 20, 2015.

(30) Foreign Application Priority Data

Jul. 19, 2016   (CA) ...................................... 2936472

(51) Int. Cl.
*A61C 7/14*    (2006.01)
*A61C 7/00*    (2006.01)

(52) U.S. Cl.
CPC .............. *A61C 7/146* (2013.01); *A61C 7/002* (2013.01)

(58) Field of Classification Search
CPC .. A61C 7/02; A61C 7/146; A61C 7/06; A61C 7/002; A61C 7/306; A61C 7/36; A61C 3/00; A61F 5/566

(Continued)

(56) References Cited

U.S. PATENT DOCUMENTS 1,597,529 A * 8/1926 Leonard ................... A61C 7/00
                                                            433/19
3,178,820 A * 4/1965 Kesling .................... A61C 7/08
                                                           128/861

(Continued)

FOREIGN PATENT DOCUMENTS

DE      102011085915 A1 *  5/2013  ............. A61C 7/002

*Primary Examiner* — Nicholas Lucchesi
*Assistant Examiner* — Shannel Wright
(74) *Attorney, Agent, or Firm* — Kyle R. Satterthwaite; Ryan W. Dupuis; Ade & Company Inc.

(57) ABSTRACT

An orthodontic direct bonding stent facilitates ideal positioning of physical attachments on a patient's teeth. Novel designs of direct bonding stents include uniquely configured windows for guiding placement of the attachments. Windows of reduced depth leave a majority of each attachment exposed beyond the stent for easy grip and manipulation, and use of a reduced height wall opposite the window-equipped wall eases removal of the stent without disruption of the adhered attachments. Use of elastomeric material at the window boundaries provides an improved seal with the tool for less adhesive splay, and inter-arch stents enable maxillary and mandibular placement with a single appliance. Lingual windows enable lingual placement of attachments for reduced visibility, and reduced wall thickness between adjacent windows provides improved mesial access to attachments. Enlarged bypass openings accommodate previously placed attachments, and bridged voids provide improved access and visibility for adhesive cleanup and accurate placement.

18 Claims, 9 Drawing Sheets

(58) Field of Classification Search
USPC .................................... 433/3, 6; 29/896.11
See application file for complete search history.

(56) References Cited

U.S. PATENT DOCUMENTS

| | | | | |
|---|---|---|---|---|
| 4,501,554 | A * | 2/1985 | Hickham | A61C 7/146 433/24 |
| 4,830,612 | A * | 5/1989 | Bergersen | A61C 7/08 433/24 |
| 5,011,405 | A * | 4/1991 | Lemchen | A61C 13/0003 433/229 |
| 6,126,443 | A * | 10/2000 | Burgio | A61C 19/066 433/215 |
| 6,231,337 | B1 * | 5/2001 | Boyd | A61C 7/08 433/6 |
| 6,241,518 | B1 * | 6/2001 | Sullivan | A61F 5/566 128/861 |
| 7,056,115 | B2 | 6/2006 | Phan et al. | |
| 7,252,509 | B2 * | 8/2007 | Sachdeva | A61C 7/146 433/229 |
| 7,578,673 | B2 | 8/2009 | Wen et al. | |
| 7,600,999 | B2 | 10/2009 | Knopp | |
| 7,658,610 | B2 | 2/2010 | Knopp | |
| 7,971,591 | B2 * | 7/2011 | Jansheski | A61C 7/08 128/848 |
| 8,496,473 | B2 | 7/2013 | Phan et al. | |
| 8,734,149 | B2 | 5/2014 | Phan et al. | |
| 8,936,463 | B2 * | 1/2015 | Mason | A61C 7/002 128/861 |
| 2004/0166462 | A1 * | 8/2004 | Phan | A61C 7/146 433/24 |
| 2004/0229185 | A1 * | 11/2004 | Knopp | A61C 7/146 433/24 |
| 2004/0253562 | A1 * | 12/2004 | Knopp | A61C 7/146 433/24 |
| 2005/0233276 | A1 * | 10/2005 | Kopelman | A61C 7/08 433/3 |
| 2005/0239013 | A1 * | 10/2005 | Sachdeva | A61C 7/146 433/24 |
| 2006/0110698 | A1 * | 5/2006 | Robson | A61F 5/566 433/6 |
| 2010/0216083 | A1 * | 8/2010 | Grobbee | A61C 7/146 433/3 |
| 2010/0227289 | A1 * | 9/2010 | Farrell | A61C 7/08 433/6 |
| 2011/0030704 | A1 * | 2/2011 | Hanna | A61C 7/08 128/861 |
| 2013/0071801 | A1 * | 3/2013 | Lanfried | A61C 13/01 433/6 |
| 2013/0273488 | A1 * | 10/2013 | Moss | A61C 7/002 433/3 |
| 2015/0157421 | A1 * | 6/2015 | Martz | A61C 7/08 433/6 |
| 2015/0250642 | A1 * | 9/2015 | Miquel | A61C 7/36 128/848 |
| 2015/0257856 | A1 * | 9/2015 | Martz | A61C 7/14 433/6 |
| 2016/0074139 | A1 * | 3/2016 | Machata | A61C 7/146 433/3 |
| 2016/0095670 | A1 * | 4/2016 | Witte | A61C 7/146 433/3 |
| 2016/0120620 | A1 * | 5/2016 | Tairaku | A61C 7/08 433/6 |
| 2016/0228214 | A1 * | 8/2016 | Sachdeva | A61C 7/002 |
| 2017/0065373 | A1 * | 3/2017 | Martz | B33Y 50/00 |

* cited by examiner

← Distal          Mesial →

STENTS FOR PLACEMENT OF ORTHODONTIC ATTACHMENTS, AND METHODS OF PRODUCING AND USING SUCH STENTS

CROSS REFERENCE TO RELATED APPLICATIONS

This application claims benefit under 35 U.S.C. 119(e) of Provisional Application No. 62/243,837, filed Oct. 20, 2015 and Provisional Application No. 62/299,634, filed Feb. 25, 2016, and claims benefit under 35 U.S.C. 119(a) of Canadian Patent Application filed Jul. 19, 2016 under the same Applicant and title as the present application. Each of the forgoing applications is incorporated herein by reference in its entirety.

FIELD OF THE INVENTION

The present invention relates generally to orthodontics. More specifically, the present invention relates to a direct bonding appliance system that increases the accuracy and efficiency of bonding attachments to teeth for orthodontic purposes.

DESCRIPTION OF THE RELATED ART

Any discussion of the prior art throughout the specification should in no way be considered as an admission that such prior art is widely known or forms part of common general knowledge in the field.

By convention, orthodontic attachments (such as brackets) may be bonded directly to the patient's teeth. To facilitate bonding, the tooth surface is prepared (etched), and a bonding agent is placed. Adhesive is then placed on the base of each attachment, which in turn is then placed on the selected tooth surface (facial or lingual). Prior to curing (completing the bond), the attachment may be repositioned (moved along the tooth surface) to a preferred location on the tooth. Once the location of the attachment is determined to be satisfactory, the adhesive is cured (bonding the attachment to the tooth).

Many challenges exist whilst utilizing the aforementioned technique. Assessing the optimal position for attachment placement intra-orally (where views are obstructed) is difficult. Contamination of the bonding surface by the contents of the patient's oral cavity must also be controlled. Therefore employing "moisture control" appliances further restricts the operator's access/view. This restricted access renders optimal placement of attachments near impossible to achieve. Ergonomics are also not favourable, as the operator must often contort their body to access (view) tight/crowded areas. Ultimately, these restrictions impair the accuracy of the attachment placement, and also extend the time required to satisfactorily bond attachments on the teeth.

Attempts have been made to mitigate these challenges. For example, Align Technology Inc. has proposed a template having openings or windows therein for guided placement of orthodontic brackets in family of U.S. patents including U.S. Pat. No. 7,056,115, U.S. Pat. No. 7,578,673, U.S. Pat. No. 7,600,999, U.S. Pat. No. 7,658,610, U.S. Pat. No. 8,496,473 and U.S. Pat. No. 8,734,149. However, several limitations of the prior art prevent optimal (most accurate and efficient) direct bonding of orthodontic attachments to teeth from being achieved.

The 'template' designs of the prior art use thermal forming dental material, which may fail to produce an intimate cohesive seal at the template to tooth interface due to the rigidity of the final template product. The resulting space between the template and teeth allows excess adhesive on the orthodontic attachment to "splay" under the template tray upon seating. This presents an issue with removing the excess adhesive prior to curing, or worse it creates more laborious work to remove the excess adhesive after curing (and after template removal).

The 'template' designs of the prior art may also fail to produce an intimate cohesive seal at the template-to-attachment interface. The "attachment support edge" will not adapt to provide a clear positive "vertical stop" when placing the orthodontic attachments. That is, the potential space left between the tooth and the template at the perimeter of the window at the closed end thereof may allow the attachment to partially slip into this space, i.e. slide slightly past the proper target position.

The 'template' designs of the prior art extend past the attachment base gingivally. Assessment of "attachment seating" is more challenging when the template extends gingivally past the attachment base. That is, once the attachment has been inserted into the respective window, access to the perimeter of the attachment to test the interface between the tooth and the attachment is prevented or severely restricted, at least until all of the attachments have been placed and the template removed. Also, potential issues arise in this removal of the template after bonding. It has been proposed in the prior art, that increasing the 'thickness' of the template will provide better guidance to the operator when placing attachments. However, the 'template removal issues' are further exacerbated if the 'template' is made thicker/more rigid. Therefore, with the template spanning gingivally past the attachment, the operator must either sacrifice 'flexibility' in the template removal (with a thicker template), or sacrifice the 'guidance' (ease of placement), of the individual attachment (with a thinner template)

The 'template' designs of the prior art do not address the utility in creating "repositioning appliances". Orthodontists by convention will often reposition multiple attachments over time to improve/achieve desired tooth movement, or place attachments on surfaces where access was previously restricted by overlapping teeth.

The 'template' designs of the prior art do not address 'lingual placement' of attachments. In fact, prior art fabrication indicates removing significant portion of the lingual surface on the 'template' (aligner) to help facilitate removal. The lingual surfaces of anterior teeth (being concave in nature), and posterior teeth (below the crest of curvature), pose an issue in removal with gingival extensions reaching past the attachments.

The 'template' designs of the prior art do not address bi-maxillary or inter-arch (both top and bottom arches connected in one piece) unit advantages. The efficiency of placing attachments is substantially increased if the patient is held in biting position during bonding. Inter-arch (bi-maxillary) designs also offer significant 'moisture control' advantages that may be incorporated. Controlling contaminants (moisture) present in the oral cavity is paramount in the bonding process.

In these respects, the direct bonding system according to the present invention substantially departs from the conventional concepts and designs of the prior art, and in doing so provides an apparatus primarily developed for the purpose of increasing the accuracy, efficiency and comfort of the orthodontic direct bonding procedure.

SUMMARY OF THE INVENTION

In view of the foregoing disadvantages inherent in the known types of apparatuses in the prior art, the present invention provides a new orthodontic direct bonding system construction wherein the same can be utilized for increasing the accuracy, efficiency, and comfort of the direct bonding procedure.

The general purpose of the present invention, which will be described subsequently in greater detail, is to provide a new orthodontic direct bonding system that has many of the advantages of the prior art mentioned heretofore and many novel features that result in a new orthodontic direct bonding system which is not anticipated, rendered obvious, suggested, or even implied by any of the prior art either alone or in any combination thereof.

An orthodontic 'direct bonding stent' is disclosed to support ideal positioning of physical (real) attachments on a patient's teeth in order to facilitate orthodontic tooth movement. Novel designs of direct bonding stents are disclosed. Also, methods are disclosed for fabricating the direct bonding stents. The methods include digitizing the patient's teeth; adding virtual attachments to predetermined locations on the digitized virtual model; 3-D printing the virtual model (with virtual attachments attached) to create a physical model (with printed attachments attached), and then lab fabrication of the direct bonding stent utilizing the physical 3-D printed model. Another method discussed involves creation of the stent virtually and fabrication utilizing additive manufacturing technologies (such as stereolithography or 3D printing) to produce the direct bonding stent.

The direct bonding stent is designed to provide negative impressions, or partial footprints or window frames of the orthodontic attachments. These window frames act as guides for placement of real attachments at a predetermined location on the patient's tooth.

Advantages of the stent may include one or more of the following: The methods, steps, and algorithms described above that are used to form the requisite digital representation of an orthodontic direct bonding stent. Additional features, bodies, or component data files can be used in addition to the tooth files used to form said stent. The elements, or concepts of the creation methods described above can be mixed or matched. That is, a file may also be created by using some steps from one method and other steps from one or more other methods.

The stent allows orthodontic brackets to be ideally positioned on teeth more efficiently. The ideal placement may be determined physically or virtually, and the placement of the brackets can be done using a stent that is, in essence, a removable guide.

According to one aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of windows for placement of the attachments into abutment with the patient's teeth through said windows, said plurality of windows each passing through said attachment support wall in a facial-lingual direction, each having an open end at a terminal end of the attachment support wall that is situated oppositely of the arc-shaped occlusal portion in the gingival direction, and each terminating at a closed end that lies opposite to said open end and adjacent to the occlusal arch-shaped portion;

wherein a depth of each window is less than a height of the respective attachment such that the attachment support wall of the stent stops short of a gingival end of the attachment when the respective attachment is seated against the closed end of the window.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of windows each passing through said attachment support wall in a facial-lingual direction for placement of the attachments into abutment with the patient's teeth through said windows;

wherein a contact surface of the attachment support wall that is positioned for placement against the patient's teeth consists of semi-rigid material of elastomeric properties so as to provide an intimate-cohesive seal between said attachment support wall and the patient's teeth.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of windows each passing through said attachment support wall in a facial-lingual direction for placement of the attachments into abutment with the patient's teeth through said windows;

wherein the attachment support wall extends gingivally from the occlusal arch-shaped portion in two opposing directions, and the plurality of windows comprises a first set of windows situated superiorly of the occlusal arch-shaped portion for placement of respective attachments on the patient's maxillary teeth and a second set of windows situated inferiorly of the occlusal arch-shaped portion for placement of respective attachments on the patient's mandibular teeth.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof;

a plurality of windows each passing through said attachment support wall in a facial-lingual direction for placement of the attachments into abutment with the patient's teeth through said windows; and a second wall extending in the gingival direction from the arc-shaped occlusal portion along a second side thereof opposite to the attachment supporting wall, wherein the second wall is of lesser height than the attachment supporting wall in the gingival direction.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof;

a plurality of windows each passing through said attachment support wall in a facial-lingual direction for placement of the attachments into abutment with the patient's teeth through said windows; and a second wall extending in the gingival direction from the arch-shaped occlusal portion along a second side thereof opposite to the attachment supporting wall;

wherein the attachment supporting wall extends from the arch-shaped occlusal portion along a facial side thereof, the second wall extends from the arch-shaped occlusal portion along a lingual side thereof, and the second wall is shaped to terminate short of a cresting point of a lingual side curvature of each tooth in a facial-lingual plane thereof.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of windows each passing through said attachment support wall in a facial-lingual direction for placement of the attachments into abutment with the patient's teeth through said windows;

wherein the attachment support wall extends from the occlusal arch-shaped portion at a lingual side thereof.

According to another aspect of the invention, there is provided a method of producing a stent for guiding placement of attachments on a patient's teeth, the method comprising, on a working model that includes physical representations of both the patient's teeth and said attachments to be placed thereon, applying a flowable material over the physical representations of the patient's teeth in a manner conforming closely against the physical representations of the attachments, without facially covering said physical representations of the attachments, whereby setting or curing of the flowable material creates a stent in which negative impressions of the physical representations of the attachments create windows passing fully through the stent in lingual-facial directions to accommodate placement of the attachments against the patient's teeth at prescribed positions thereon through the windows, whose positions on the stent are dictated by positions of the physical representations of the attachments in the working model.

According to another aspect of the invention, there is provided a method of placing attachments on a patient's teeth, the method comprising:

obtaining a stent that has been custom-fabricated for said patient's teeth and, that comprises semi-rigid material of elastomeric properties, and that comprises windows therein for guided placement of said attachments to the patient's teeth through said stent;

positioning the stent on the patient's teeth in a manner placing the semi-rigid material in cohesively and intimately sealed contact with the patient's teeth at a perimeter of each window;

adhering each attachment to the patient's teeth through a respective one of said windows, during which splaying of the adhesive out from beneath the attachments is prevented by the cohesively and intimately sealed contact between the stent and the patient's teeth.

According to another aspect of the invention, there is provided a stent for use in repositioning of select attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of windows each passing through said attachment support wall in a facial-lingual direction for placement of the select attachments into abutment with the patient's teeth through said windows; and bypass openings in the support wall that pass fully therethrough in the facial-lingual direction and that open into the support wall from a terminal end of the attachment support wall that is situated oppositely the occlusal arch-shaped portion in the gingival direction, each bypass opening being larger than the windows so as to space the stent away from other existing attachments on the patient's teeth that are not being repositioned during repositioning of the select attachments.

According to another aspect of the invention, there is provided a method of producing a stent for guiding placement of attachments on a patient's teeth, the method comprising using computerized means to:

producing a virtual model that includes a virtual dentition that is representative of the patient's teeth and virtual objects that are representative of the attachments to be placed on the patient's teeth and have been virtually positioned on the virtual dentition at desired target locations for the attachments;

adding a virtual stent to the virtual model, including customizing a shape of a support wall the virtual stent to include virtual windows therein that reside at the target locations occupied by the virtual objects and that open through the support wall of the stent in a facial-lingual direction; and from the virtual stent, producing a physical stent in an automated additive manufacturing process, whereby the physical stent features actual windows corresponding to the virtual windows of the virtual stent for use in guiding placement of the attachments on the patient's teeth via said windows.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of windows for placement of the attachments into abutment with the patient's teeth through said windows, said plurality of windows each passing through said attachment support wall in a facial-lingual direction, each window having an open end at an originating end of the attachment support wall where said attachment support wall joins with the arc-shaped occlusal portion, and each window terminating at a closed end that lies opposite to said open end in an occlusal-gingival direction.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of windows for placement of the attachments into abutment with the patient's teeth through said windows, said plurality of windows each passing through said attachment support wall in a facial-lingual direction and each having a depth measured between an open end of the window and an opposing closed end thereof in a gingival-occlusal direction;

wherein at least one posteriorly located window is deeper in the gingival-occlusal direction at a distal side of said posteriorly located window than at an opposing mesial side thereof to improve access to said posteriorly located window from the mesial side during placement of the respective attachment in said posteriorly located window.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of windows for placement of the attachments into abutment with the patient's teeth through said windows, said plurality of windows each passing through said attachment support wall in a facial-lingual direction;

wherein the support wall comprises at least one interdental area of reduced lingual-facial thickness that is located between a respective pair of adjacent windows and slopes distally and gingivally toward a more posterior one of said respective pair of adjacent windows for improved mesial access to said more posterior one of said pair of adjacent windows.

According to another aspect of the invention, there is provided a stent for guiding placement of attachments on a patient's teeth, the stent comprising:

an occlusal arch-shaped portion for fitting against occlusal surfaces of the patient's teeth; and an attachment support wall extending in a gingival direction from the arc-shaped occlusal portion along one side thereof; and a plurality of voids in said attachment support wall, each void passing through said attachment support wall in a facial-lingual direction;

a respective bridge portion of the attachment support wall spanning across each void at a gingival side thereof opposite the occlusal arch-shaped portion for seating of a respective attachment against said bridge portion at a gingival side thereof opposite the void;

wherein a tooth-facing side of each respective bridge portion is spaced outwardly from a tooth-facing side of an occlusal portion of the attachment support wall that lies across said void from the respective bridge portion and joins with the occlusal arch-shaped portion, whereby in a worn position of the stent, each bridge portion is spaced outward from a respective tooth against which the tooth-facing side of the respective occlusal portion of the attachment support wall is abutted.

According to another aspect of the invention, there is provided a method of placing one or more attachments on a patient's teeth, the method comprising:

obtaining a stent having:
an occlusal arch-shaped portion for fitting against occlusal surfaces of the patient's teeth;
a support wall extending in a gingival direction from the arc-shaped occlusal portion along one side thereof; and
a plurality of voids in said attachment support wall, each void passing through said attachment support wall in a facial-lingual direction; and a respective bridge portion of the attachment support wall spanning across each void for seating of a respective attachment against said bridge portion at a side thereof opposite the void;

positioning the stent in a worn position on the patient's teeth, and thereby placing each bridge portion at a location spaced outward from a respective tooth to leave a gap between said bridge portion and said respective tooth;

placing a base of a selected attachment against the respective tooth in a position seating the attachment against the respective bridge portion at said location spaced outwardly from the respective tooth, from which the attachment reaches inward to the respective tooth across said gap.

According to another aspect of the invention, there is provided a method of placing one or more attachments on a patient's teeth, the method comprising:

obtaining a stent having:
an occlusal arch-shaped portion for fitting against occlusal surfaces of the patient's teeth; and
an attachment support wall extending in a gingival direction from the arc-shaped occlusal portion along one side thereof; and
a plurality of windows for placement of the attachments into abutment with the patient's teeth through said windows, said plurality of windows each passing through said attachment support wall in a facial-lingual direction, each having an open end and an opposing closed end;

positioning the stent in a worn position on the patient's teeth, and thereby placing the closed end of each window at a location spaced outward from the respective tooth to leave a gap between said closed end of the window and said respective tooth; placing a base of a selected attachment against the respective tooth in a target position seating the attachment against the closed end of the respective window at said location spaced outwardly from the respective tooth, from which the attachment reaches inwardly to the respective tooth across said gap.

DESCRIPTION

Figure 1:
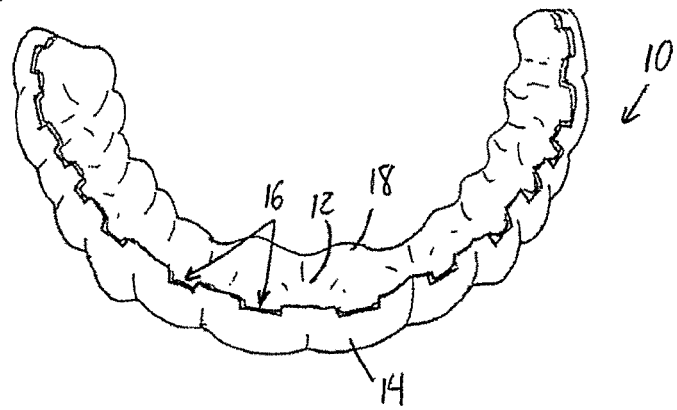
FIG. 1A-C shows frontal, sagittal, and transverse views of an Intra-arch (Facial) direct bonding stent designed for placement of attachments on the facial surface of teeth of a single arch.
Figure 1:
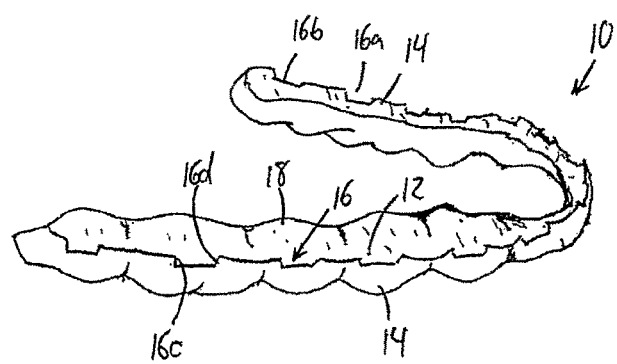
Figure 1:
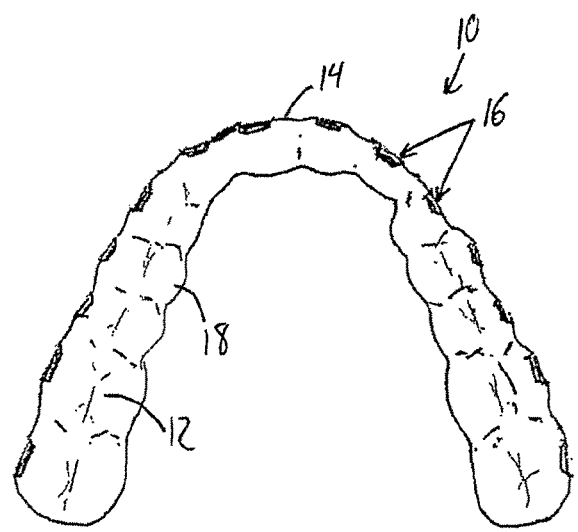

FIG. 1 shows one embodiment of a direct bonding stent. The stent 10 has the appearance of a removable appliance; however, it has geometrical features resembling partial 'window frames' or 'partial footprints' (negative impressions) to guide the placement of an attachment on a given tooth surface.

This intra-arch (Facial) direct bonding stent 10 is designed to place attachments on the facial (cheek side) of teeth. Therefore, a significant portion of the lingual surface of the tooth is not covered by the stent to help facilitate removal. The lingual surfaces of anterior teeth (being concave in nature), and posterior teeth (below the crest of curvature), pose an issue in removal with gingival extensions reaching past the attachments.

More specifically, the first embodiment stent 10 features an occlusal arch-shaped portion 12 for fitting conformingly against occlusal surfaces and incisal edges of the patient's maxillary or mandibular teeth in an occlusal plane. Along an outer facial side of the occlusal arch-shaped portion 12, an attachment support wall 14 extends therefrom in a gingival direction, either superiorly or inferiorly depending on whether the stent 10 is intended for the maxillary of mandibular arch of the patient. At discrete positions along the arch-shaped path followed by the support 14 wall, a plurality of window-like openings 16 pass through the support wall 14 in a facial-lingual direction, each being bordered on three sides by a respective one of the aforementioned 'window frames'. Each window 16 has an open end 16a at a terminal edge of the support wall 14 that lies opposite to the occlusal arch-shaped portion 12 in the gingival direction. Each window 16 terminates at a closed end 16b that lies opposite of the open end at a location adjacent to the occlusal plane in which the arch-shaped portion 12 resides. By adjacent, it is meant that the closed end 16b of the window resides nearer to the occlusal plane than the open end of the window. The closed end 16b of the window denotes one of the three sides of the respective window frame that delimits the area of the window. At this closed end of the window, a thickness of the support wall 14 defines an 'attachment support edge' against which a respective attachment is abutted during use of the stent to define a properly attained position at which the attachment is to be adhered to the respective tooth. Two opposing sides 16c, 16d of the window extend perpendicularly from opposite ends of the 'attachment support edge' to join up with the terminal end of the support wall 14 at the open end 16a of the window, thereby completing the respective three-sided window frame.

The width of each window 16 between its two sides closely matches the width of a respective attachment whose placement on the patient's tooth is to be guided by said window during use of the stent. On the other hand, a depth of each window 16 measured from the open end 16a thereof at the terminal edge of the support wall 14 to the opposing closed end 16b is less than the corresponding height measurement of the attachment from a gingival end thereof to an occlusal/incisal end thereof. The gingival end refers to an end of the attachment that resides nearest to the patient's gingiva in the final adhered position of the attachment on the patient's tooth, while the occlusal/incisal end of the attachment refers to the end of the attachment nearest to the biting edge (incisal edge) or biting surface (occlusal surface) of the tooth. In the preferred embodiment, the depth of the window 16 is approximately equal to one-third of the attachment height. Placement of the respective attachment into the window 16 with the sides and incisal/occlusal end of the attachment closely adjacent the closed end and sides of the window sets the attachment in the target position on the patient's tooth. In this properly seated position of the attachment, with the gingival two-thirds of the attachment reach out of the window into an exposed outside the confines of the stent. That is, the respective window surrounds only the incisal/occlusal third of the attachment.

Window frames may also feature contrasting coloration or distinctive markings on the stent surface. The purpose of the contrasting coloration or markings is to further illuminate the stent position thereby increasing the clinician's ability to visualize of the stent window frame intra-orally. The contrasting coloration may also aid in assessment and determination of full seating of the attachment. Both of the aforementioned advantages increase the speed and efficiency of attachment placement.

Figure 8:
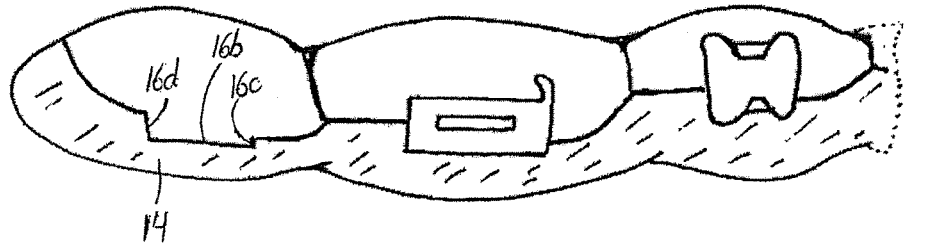
FIG. 8 shows a close-up sagittal view of an Intra-ach direct bonding stent in which the windows for posterior teeth have reduced mesial sides for improved mesial access to the windows during placement of attachments therein.

With reference to FIG. 8, the stent window frame may also have a portion of the mesial or distal aspect of the support wall removed, resulting in a shorter window depth at one side of the window than in the other embodiments. In FIG. 8 the mesial support wall 16c of the window is shorter in order to facilitate placement of the attachment. For example, when placing attachments on posterior teeth, removal of a portion of support wall at the mesial (anterior) side of the window in a manner reducing the support wall height at this mesial side of the window allots the clinician more access to position the attachment into the appropriate position. This design modification may also involve increasing the occlusal-gingival height of the support wall at the opposing distal side 16d of the window relative to the earlier embodiments in order to allow a more positive horizontal stop when positioning the attachment. Accordingly, the support wall and related window depth at the distal side of the window may be greater those at the mesial side of the window, as shown in FIG. 8. In the fully seated position of the attachment, it abuts against the taller distal side 16d of the window and the closed end 16b of the window. The depth of the window at the taller distal-side 16d is again preferably about one third of the height of the expected attachment, while the reduced mesial side 16c of the window is shallower to provide increased mesial access to the window and attachment during placement of the attachment into the properly seated position. In FIG. 8, the most-posterior window is shown unoccupied to illustrate the shallower/shorter mesial side 16c of the window versus the deeper/taller distal side 16d of the window, while the other two illustrated windows are shown with respective attachments fully seated therein. Another advantage of this modification is improved visual access to the window at the mesial side thereof to assess positive attachment seating.

Concurrent to the reduction of the support wall at the mesial side of the windows, removal or scalloping of the stent material inter-dentally (i.e. at the area between adjacent teeth in the same arch) to improve access even further may also be incorporated into stent designs. Such scalloping or removal reduces the lingual-facial thickness of the stent's support wall at these inter-dental areas. The scalloping or removal is performed in manner creating a respective sloped channel that slopes distally and gingivally toward the mesial side of a more-posterior one of the two windows between which this inter-dental area resides. The attachment can be inserted into the more posteriorly situated window via this channel in a sloped gingival/distal direction to pass the attachment over the reduced-height mesial area of the support wall area at the mesial side of the window, whereby the channel of reduced lingual-facial thickness improves mesial access to the window. The smoothly and concavely curved cross-sectional profile of a scallop-like channel that widens toward the outer surfaces of the surrounding thicker areas of the support wall minimizes impedance to smooth passage of the attachment through the channel toward the more posteriorly situated window.

The direct bonding stents of the preferred embodiments are fabricated from semi-rigid materials with elastomeric properties (such as the addition cured silicones, 'Tango™' family or other SLA elastomeric resins) to produce an intimate cohesive seal at the stent-to-tooth interface. This seal prevents excess adhesive on the orthodontic attachment from "splaying" under the stent upon seating of attachment against the tooth. An intimate cohesive seal is also produced at the stent-to-attachment interface. The "attachment support edge" is able to more closely adapt to the attachment to provide a clear positive "vertical stop" when placing the orthodontic attachments. That is, the intimate cohesive seal between the support wall 14 at the boundaries or window frame of each window 16 maintains the attachment support edge at the closed end 16b of the window in directly adjacent relation to the facial surface of the tooth, whereby the inserted attachment cannot slip between the stent and tooth out of the targeted alignment. Therefore the accuracy and efficiency in placing the attachments with the stent is increased, as the provider can also tactilely "feel" the correct attachment position in the stent window frame (as the attachment fits in the negative impression).

Once the attachment is seated, attachment placement/seating forces cannot displace the stent, as the sealed condition of the stent against the patient's dentition resists flexing or displacing of the stent out of position, thereby maintaining the positional integrity of the window during placement of the attachment. This reinforces the positive "vertical stop" to aid in placement. There is also a more accurate transfer of the attachment to the tooth, as there is no displacement when seating the attachment.

As described above, the stent 'window frames' terminate prior to the gingival two-thirds of the attachment. This early termination ensures 'passive removal' of the stent from the dentition. No lifting of the gingival end of the support wall 14 away from the facial surfaces of the teeth is required to clear the adhered attachments during removal of the stent. Therefore, no concerns exist regarding inadvertent "debonding" (bond failure) of the attachments when removing the stent. Also, assessment of "attachment positive seating" on the tooth is more efficient with the partial height 'stent window.' Each side of the attachment is readily accessible over a majority of its length in order to assess the seating of the attachment and/or test the bonding of the attachment to the tooth prior to removal of the stent, whereby any necessary repositioning and re-seating of the attachment can be performed without removal of the stent from the patient.

A second wall 18 of the stent extends gingivally from the occlusal arch-shaped portion 12, just like the attachment support wall 14. However, unlike the attachment support wall 14, the second wall 18 extends along the inner or lingual side of the occlusal arch-shaped portion 12, and has a reduced height in the gingival direction relative to the height of the attachment support wall 14. Lying opposite to the support wall 14 that conforms against the facial surface of the patient's teeth, the second wall 18 thus conforms against the lingual surface of the patient's teeth. Being of lesser height, the second wall 18 spans less of each tooth in the gingival direction than the support wall 14, and terminates prior to a point at which the concave curvature of the lingual surface of each tooth crests in a facial-lingual plane.

Figure 2:
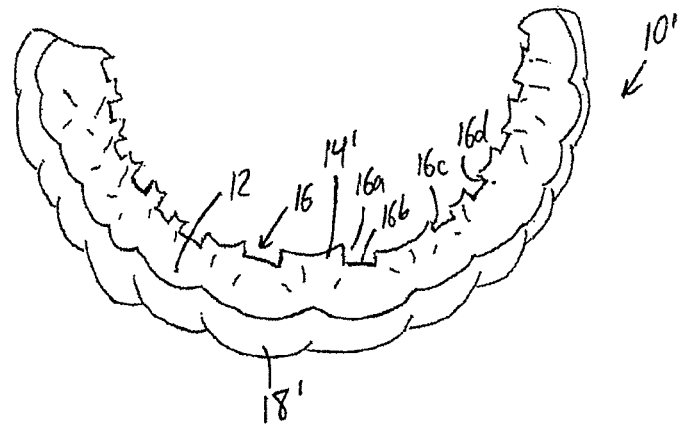
FIG. 2A-C shows frontal, sagittal, and transverse views of an Intra-arch (Lingual) direct bonding stent designed for placement of attachments on the lingual surface of teeth of a single arch.
Figure 2:
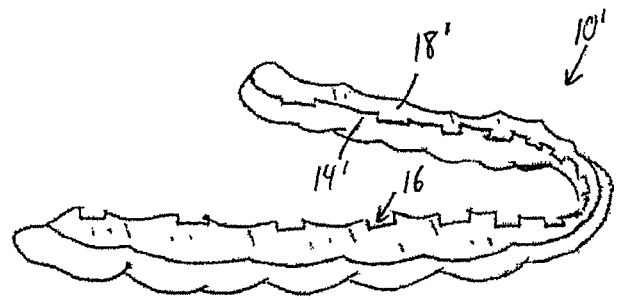
Figure 2:
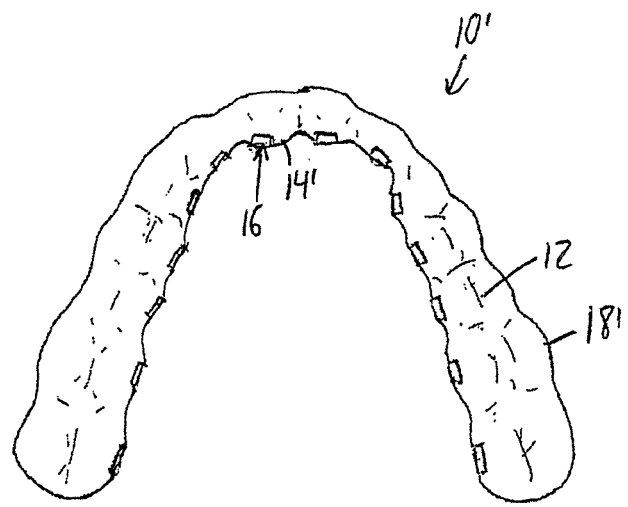

FIG. 2 shows another embodiment of a direct bonding stent 10'. Whereas the stent 10 of the first embodiment has the attachment support wall on the facial side of the arch to enable placement of attachments on the facial surface of the patient's teeth, the intra-arch (Lingual) direct bonding stent 10' of the second embodiment is designed to place attachments on the lingual (tongue side) of teeth. The second embodiment stent 10' shares many of the same properties as the intra-arch (Facial) version of the stent; however, a significant portion of the facial surface of the tooth is not covered by the stent in order to help facilitate removal. That is, in the second embodiment, the shorter second wall 18' resides on the outer/facial side of the arch for mating with the facial surfaces of the teeth in a position lying opposite to the lingually-located support wall 14'. As with the first embodiment, the stent 'window frames' terminate prior to the gingival two-thirds of the attachment, which also helps facilitate removal as the lingual surfaces of teeth (being concave in nature) would pose an issue in removal of the stent if the support wall 14' were to extend further in the gingival direction and span the full attachment height in the gingival direction.

Figure 7A:
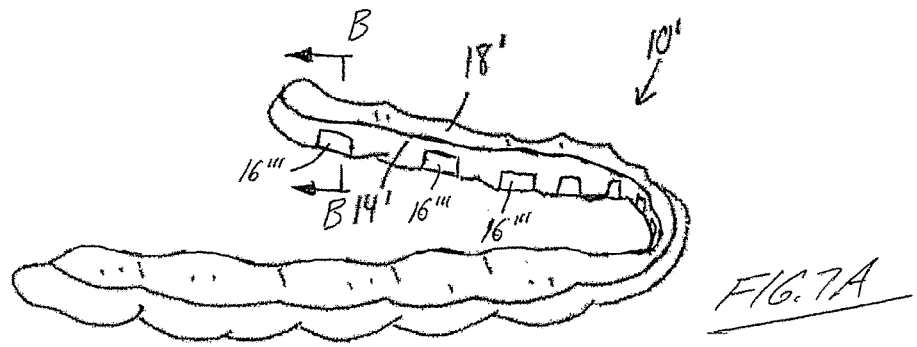
FIG. 7A shows a sagittal view of an Intra-arch (lingual) direct bonding stent which differs from that of FIG. 2 in that the windows of the stent in which the attachments are to be placed during use are inversed relative to the embodiment of FIG. 2.
Figure 7B:
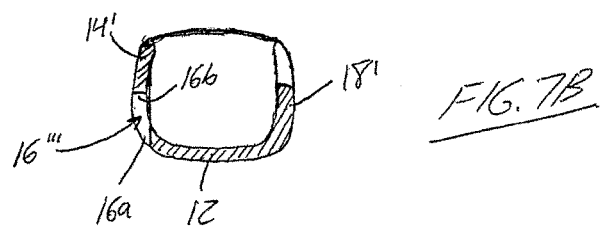
FIG. 7B shows a cross-sectional view of the Intra-arch (lingual) direct bonding stent of FIG. 7A, as viewed along line B-B thereof.

With reference to FIG. 7, a modification to the intra-arch lingual stent's window orientation may useful for maxillary or mandibular lingual stents when placing anterior attachments. In this embodiment, the stent window 16''' is oriented with the open end 16a of the window directed towards the incisal or occlusal surface instead of toward the gingiva. The open end 16a of the window 16''' thus resides at the originating end of the support wall 14' that joins to the arc-shaped occlusal portion 12 of the stent, and the closed end 16b of the window 16''' resides intermediately between the originating and terminal ends of the support wall so that the window 16''' terminates short of the opposing terminal end of the support wall 14'. The attachment is thus inserted into the window in a gingival direction through the occlusally-facing open end 16a of the window. These occlusally-open lingual-side windows 16''' are deeper than the gingivally-open windows of the preceding embodiment since the full height of the attachment must be receivable in the window so that the seated attachment resides fully past the occlusal plane of the tooth in the gingival direction. This inverted orientation of the windows on the lingual side of the intra-arch lingual bonding stent aids in positioning the attachments using indirect vision, and increases ease of placement. Removal of the stent remains passive as the posterior occlusal aspect of the stent may be unseated, moved posteriorly, and then rotated (superiorly or inferiorly) without placing strain on the bonded attachments.

Figure 3:
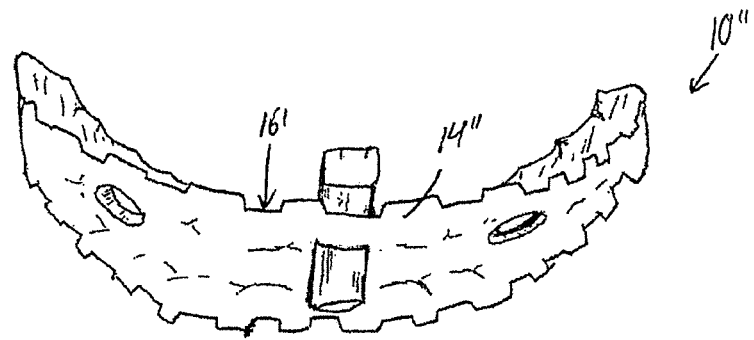
FIG. 3A-C shows frontal, sagittal, and transverse views of an Inter-arch (Facial) direct bonding stent designed for placement of attachments on the facial surface of teeth of both maxillary and mandibular arches.
Figure 3:
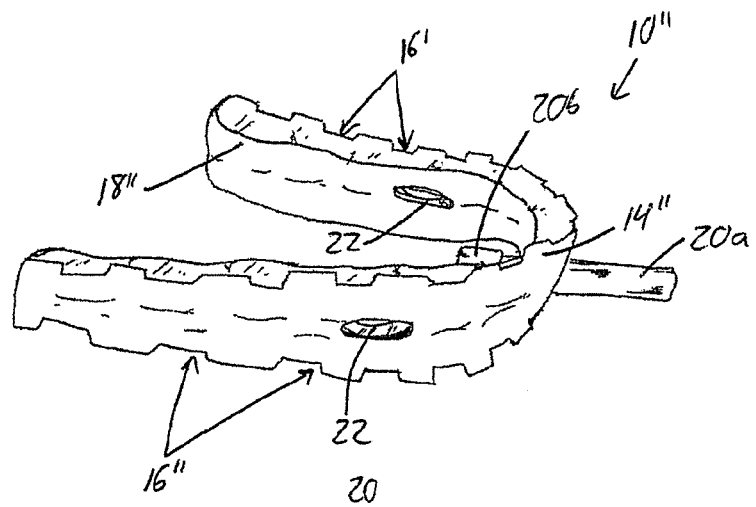
Figure 3:
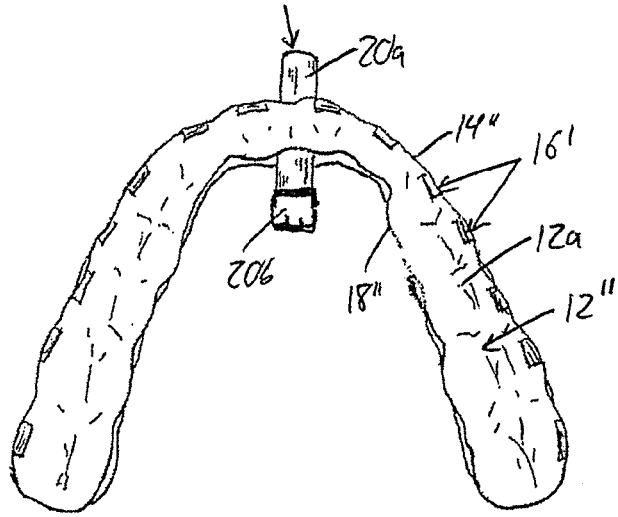

FIG. 3 shows another embodiment of a direct bonding stent 10". This inter-arch (Facial) direct bonding stent is designed to place attachments on the facial (cheek side) of teeth. The stent shares many of the same properties as the preceding embodiments, however, both top-arch (maxillary) and bottom-arch (mandibular) stents are connected in a one-piece unit. In this case, the support wall 14" and the shorter second wall 18" each extend both superiorly and inferiorly from a shared occlusal arch-shaped portion 12" in the gingival directions of the respective dental arches. The upper surface 12a of the shared occlusal arch-shaped portion 12" is shaped to conform to the occlusal surfaces and incisal edges of the patient's maxillary teeth, while the lower surface of the shared occlusal arch-shaped portion 12" is shaped to conform to the occlusal surfaces and incisal edges of the patient's mandibular teeth. A first set of windows 16' is defined at a superior terminal end of the support wall 14" for use in placement of attachments to the patient's maxillary teeth, while a second a second set of windows 16" is defined at an inferior end of the support wall 14" for use in placement of attachments to the patient's mandibular teeth.

This design of the third embodiment offers several advantages. The efficiency of placing attachments is substantially increased if the patient is held in biting position during bonding (reduced patient jaw movement). Inter-arch (bi-maxillary) designs also offer significant 'moisture control' advantages that may be incorporated. An example of these moisture control features is shown in the form of a length of suction tubing 20 that perforates the shared occlusal arch-shaped portion 12" of the stent (inter-arch) 10" to enter the lingual portion of the oral cavity (tongue side). A connection portion 20a of the tubing 20a extends from an anterior apex of the shared occlusal arch-shaped portion 12" to enable coupling of a suitable vacuum source to the tubing 20a outside the oral cavity. An internal passage of the tubing extends anteriorly through the connection portion 20a, and onward through the shared occlusal arch-shaped portion 12" of the stent in the facial-lingual direction, where the passage continues through an internal cavity portion 20b of the tubing that reaches posteriorly into the oral cavity at the center of the arch-shaped stent. This tubing may be configured in a variety of formations (both in number and position), and may also be attached/fixed to the lingual portion of the stent. Controlling contaminants (moisture) present in the oral cavity is paramount in the bonding process, and the tubing 20 enables suction of excess moisture from the oral cavity through the stent during bonding. Other inter-arch perforations may also be present in stent design to help facilitate patient respiration, for example as shown by the presence of two respiration passages 22 perforating the shared occlusal arch-shaped portion 12" in the facial-lingual direction on either side of the centrally located suction tube 20. Inter-arch designs may also incorporate buccal mucosa isolation ('cheek spreading arms/wings') to further segregate the intra-oral tissues from the bonding surfaces (not shown in figures). With the 'inter-arch' stent in place, the only major source of saliva in the bonding zone of the oral cavity is the parotid gland duct (Stensen's duct). Stensen's duct is located laterally to the second maxillary molar, and may pose an issue in bonding without isolation. Therefore, buccal mucosa isolation may be employed to combat potential saliva contaminant during bonding. Likewise, other embodiments, including intra arch designs, may also incorporate buccal mucosa isolation ('cheek spreading arms/wings') to further segregate the intra-oral tissues from the bonding surfaces.

Figure 4A:
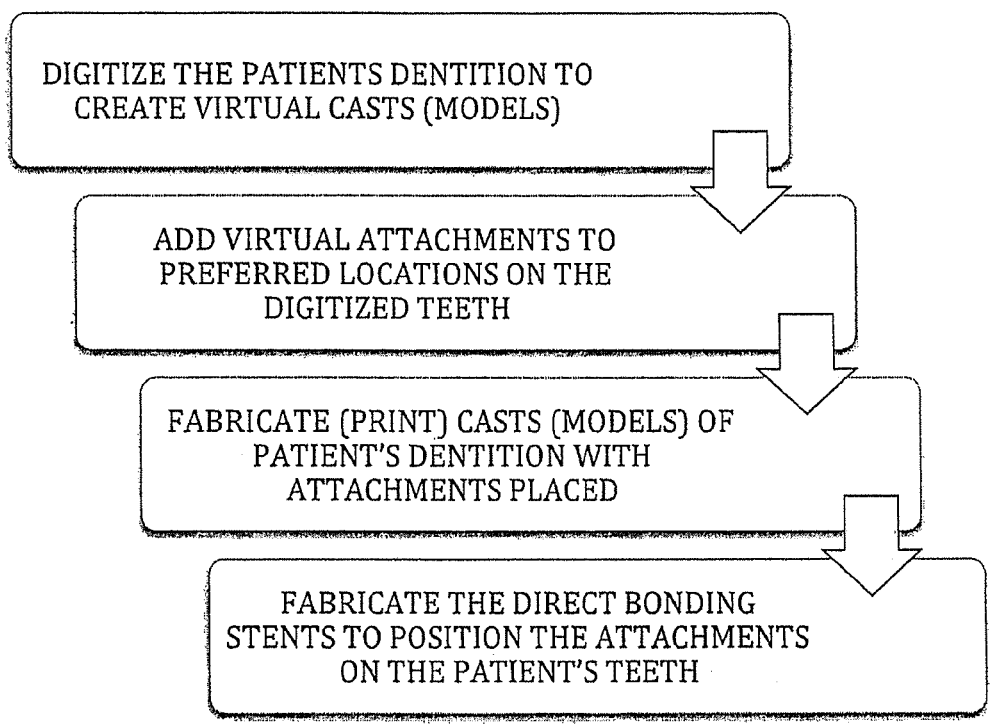
FIGS. 4A and 4B show exemplary methods or processes to fabricate a direct bonding stent to position an attachment on a patient's tooth.

FIG. 4A shows an exemplary method or process to fabricate a stent for positioning of an attachment on a patient's tooth. First, the process requires production of models of the patient's dentition. This may be accomplished utilizing physical (non-digital), or virtual (digital) means.

Historically, models have been produced by non-computer-aided techniques. Typically, impressions of the patient's dental arches are made using hydrocolloid or elastomeric materials. Replica plaster or "stone" casts (full arch models) are made from each impression and sealed.

Currently, models may be produced utilizing computer-aided techniques. In this method teeth are digitized to produce virtual models of the patient's dentition. This digitization process may be accomplished utilizing a variety of methods. For example, the patient's dentition may be scanned or imaged using well-known technology. There are a variety of reflective systems in use. Some of these reflective systems utilize non-optical incident energy sources (such as sonar or microwave radar). Others systems available utilize optical energy. Those 'non-contact-type' systems utilizing reflected optical energy further contain special instrumentation configured to allow for precise measurement recording (e.g., triangulation, imaging radar, and interferometry).

The second step in the stent fabrication process involves addition of objects/attachments (orthodontic brackets for example) to the models in preferred locations on the teeth.

If the physical cast method is utilized, the preferred positions for the objects are first determined on the stone model. Once the location has been determined, the objects are bonded to the sealed stone models using a temporary adhesive.

If the virtual model method is utilized, the preferred positions for the objects are first located on the digitized teeth (3D virtual model). The virtual models may be a computer aided design (CAD) model, or may be scanned using scanners described above. Once the location has been determined on the virtual model, the "virtual objects" are added. The virtual objects are in essence 3D models of actual physical attachments (orthodontic brackets for example) that are to be placed on the patient's teeth. The objects may be positioned on a digitized tooth using a computer or workstation having a suitable graphical user interface (GUI) and software appropriate for viewing and modifying the images. Following positioning of the objects, the virtual model (complete with objects) is converted (fabricated) into a physical model. Fabrication utilizes well-known technology (3-D printing technology) to create a non-scaled (1:1) identical physical version of the virtual model.

In either of the aforementioned methods listed, the result is production of "working models" used for laboratory fabrication of dental appliances. These working models are used to fabricate the "direct bonding stent". The working model is fabricated using "identical", "non-scaled", "non-cavitated", models and object projections. Stent fabrication involves a working model, which includes physical representations of the patient's teeth and "physical" objects attached to the modeled teeth to serve as physical representations of the actual attachments that are to be attached to the patient's actual teeth.

Stent design (i.e. intra-arch vs. inter-arch, facial vs. lingual placement, etc.) must also be selected prior to fabrication of the direct bonding stent, for example from among the three embodiments specifically described above and illustrated in FIGS. 1-3.

Finally, once the stent design has been selected, fabrication of the stent takes place. A lab technician, or automated machine process (e.g. assembly line), utilizes the working model to fabricate the direct bonding stents. Variation in fabrication process may exist, however, all embodiments encompass the following fabrication principles.

Direct Bonding Stents utilize materials with elastomeric properties (addition silicones for example) to provide an intimate/accurate fit to teeth.

The stent window frames are in effect negative impressions (partial footprints) of the object projections, not a removal or "cut out" of vacuum formed plastics.

The stent cannot be formed by pressure or vacuum forming techniques as the stent material transforms (polymerizes) from a reversible (surface wetting) state to irreversible (cohesive seal) state.

One fabrication process involves flowing polymerizable stent material (addition silicone for example) over the working model dentition (occlusal, buccal and lingual surfaces), and intimately between the teeth and object at the areas around the interface shared between the object and the modeled tooth, without fully covering the objects facially on the model dentition. Air-driven techniques may be utilized to coerce the flowable material into tight spaces, and encourage a more intimate cohesive seal. Once the material has suitably encased the objects, the stent material is cured (or allowed to set). The stent is then modified by removal of the over-extended material (now polymerized into more rigid irreversible state). During this step, around each object, any set/cured material is removed from adjacent the gingival two-thirds of the object, creating a partial window frame or footprint for accommodating the incisal/occlusal one third of the actual attachment during use of the stent. Also depending on the modeled dentition surface the object is placed on (buccal or lingual), the cured/set material from the opposite surface of the modeled dentition is removed (at the crest of the tooth curvature for example) such that only partial coverage is provided by the stent on the surface of the modeled tooth opposite that at which the objects are located. These modifications allow easier placement of attachments, and also aid in the removal of the stent following bonding.

During the fabrication process, the shared occlusal arch-shaped portion 12" of the stent may also be reinforced (with acrylic for example) to form a "bite block", or increase the dimensional stability of the direct bonding stent.

One modification to this fabrication process exists with the fabrication of the inter-arch (bi-maxillary) stent 10" of the third embodiment. This version of the direct bonding stent places the patient into a constructed bite whereby the patient's maxillary and mandibular teeth are disoccluded (opening approximately 10-15 mm). Upper and lower arches of the stent may be connected (bridged) by the same material as the stent (addition silicone), resulting in a thicker shared occlusal arch-shaped portion 12" that has the same uniform material composition as the rest of the stent. Alternatively, the bridge may be a different material (acrylic for example). In the case of the latter, the resulting shared occlusal arch-shaped portion 12" may have a multi-layered configuration of materially distinct layers, where upper and lower layers that abut the occlusal surfaces and incisal edges of the maxillary and mandibular teeth, respectively, comprise the same elastomeric material as the attachment support walls 14 of the stent, while an intermediate layer between the upper and lower layers is a more rigid material, such as acrylic. Whether the shared occlusal arch-shaped portion 12" is of singular material or multi-material construction, the bridge between the arches must be rigid, or dimensionally stable. For example, in the instance of a singular material construction, the greater thickness of the bridge, which may for example be 10-15 mm thick, compared to the thinner arch-shaped portion of the intra-arch embodiments, imparts a greater rigidity to this area of the stent, despite having the same material composition, in order to provide the required dimensional stability. The material forming the bridge may also be perforated to allow for moisture control applications (suction tubing), and improved patient oral respiration (if nasal respiration is impossible). In the case of the multi-material construction with a more rigid core or intermediate layer, the aforementioned moisture control and/or respiration passages may be provided within the more rigid intermediate layer in order to best resist closure of these passages by compressive action between the patient's maxilla and mandible.

Figure 6A:
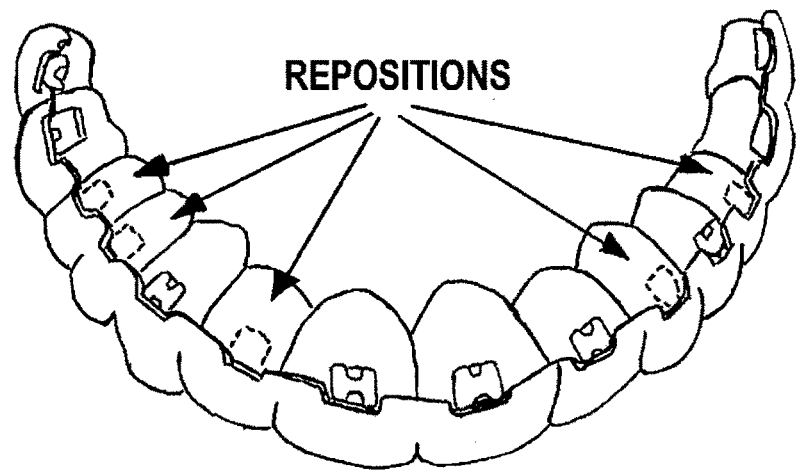
FIG. 6A shows a frontal view of an Intra-arch (Facial) direct bonding repositioning stent designed for placement of attachments on the facial surface of teeth at an intermediate attachment-repositioning phase of an orthodontic treatment timeline.
Figure 6B:
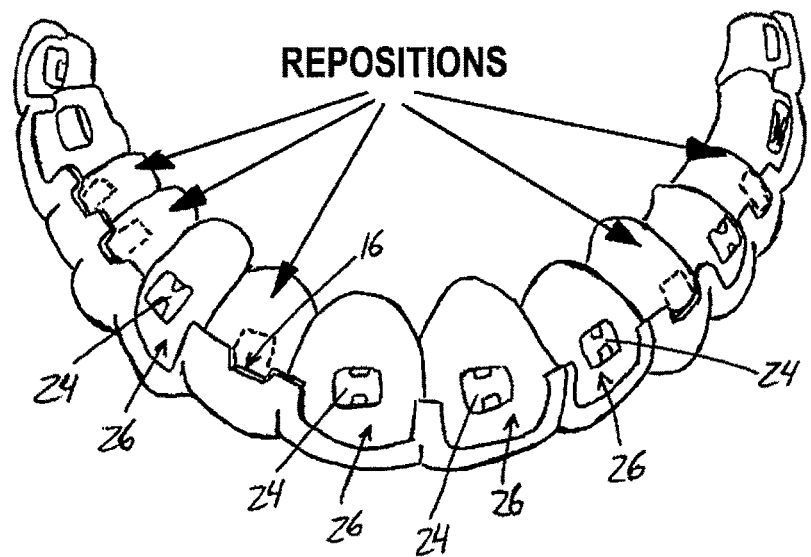
FIG. 6B shows a transverse view of an Intra-arch (Facial) direct bonding repositioning stent similar to that of FIG. 6A, but with enlarged by-pass openings in the stent to stay clear of existing attachments that are to be left in place during the repositioning of other attachments.

Another modification exists in fabrication of a mid-treatment or repositioning stent (see FIGS. 6A and 6B). At any given point in a treatment timeline, an orthodontist may wish to alter the position of some (but not all) of the attachments, and a stent may be fabricated to aid in the repositioning process. Any of the novel direct bonding stent designs may used or modified to allow for midcourse correction of attachment placement. The main advantage of the direct bonding stent design exists in the improved passive removal (due to early stent termination prior to the gingival two-thirds of the attachment). Placing the repositioning stent would be exceedingly more difficult, and the risk of accidental debonding of existing attachments would be increased, with full-length gingival extensions of the support wall. Alternatively, or additionally, the stent may be fabricated to completely by-pass the existing attachments that are present (and correctly positioned) on the patient's dentition. The direct bonding stent may be terminated occlusally to the ideally placed existing attachments, thus ensuring a completely passive removal of the direct bonding stent. This option is shown in FIG. 6B, where at areas of the stent that correspond to the positions of the existing attachments 24 that are not to be repositioned, large bypass openings 26 of greater size (in both width and depth) than the attachment-guiding windows 16 are provided so as to leave the existing attachments and surrounding areas of the tooth uncovered by the stent. When fabricating such a stent from a physical model, the bypass openings (like the windows 16) may be created either by controlling the application of the flowable material to leave voids at the intended areas of said openings, or by later trimming away the set or cured material at these areas.

Figure 4B:
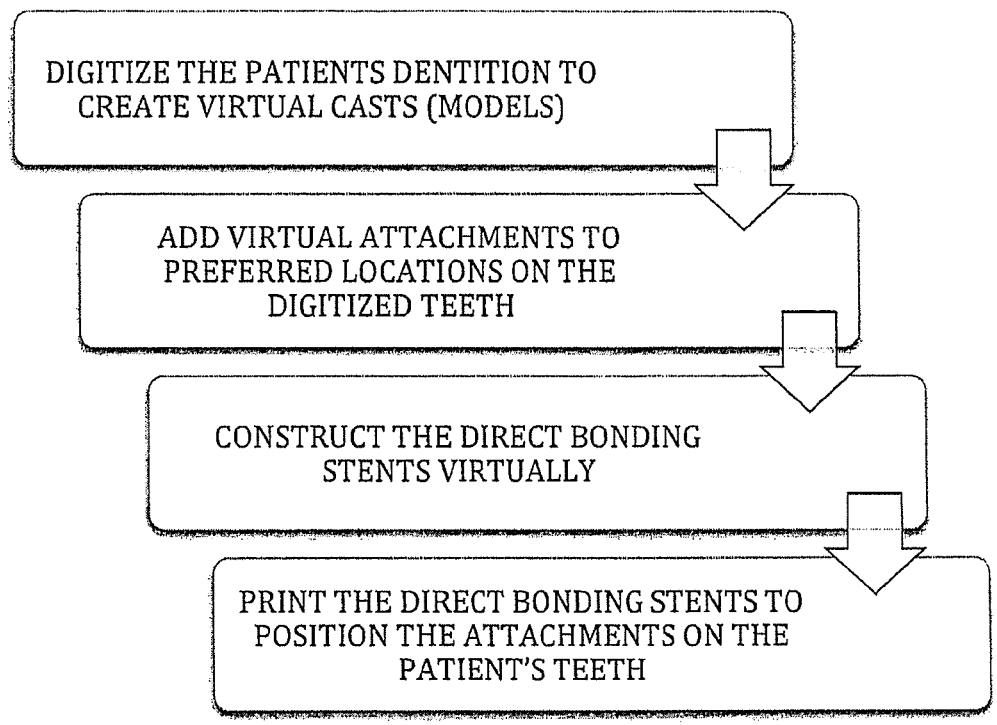

FIG. 4B shows an alternative exemplary method or process to fabricate a stent to position an attachment on a patient's tooth. In this method teeth are digitized to produce virtual models of the patient's dentition (as described in FIG. 4A). The preferred positions for the placement of objects are located on the digitized teeth (3D virtual model). Once the location has been determined on the virtual model, the "virtual objects" are added. Following addition of the objects, the virtual model (complete with objects) is used to create a "virtual stent". This virtual stent is then fabricated utilizing well-known technology such as a rapid prototyping device (stereolithography machine) to create a non-scaled (1:1) identical physical version of the virtual stent. Recent advances in stereolithographic materials (such as 'Tango™' family or other SLA elastomeric resins) that are able to simulate properties of elastomerics (rubber like properties) allow this fabrication process to be possible.

Figure 5:
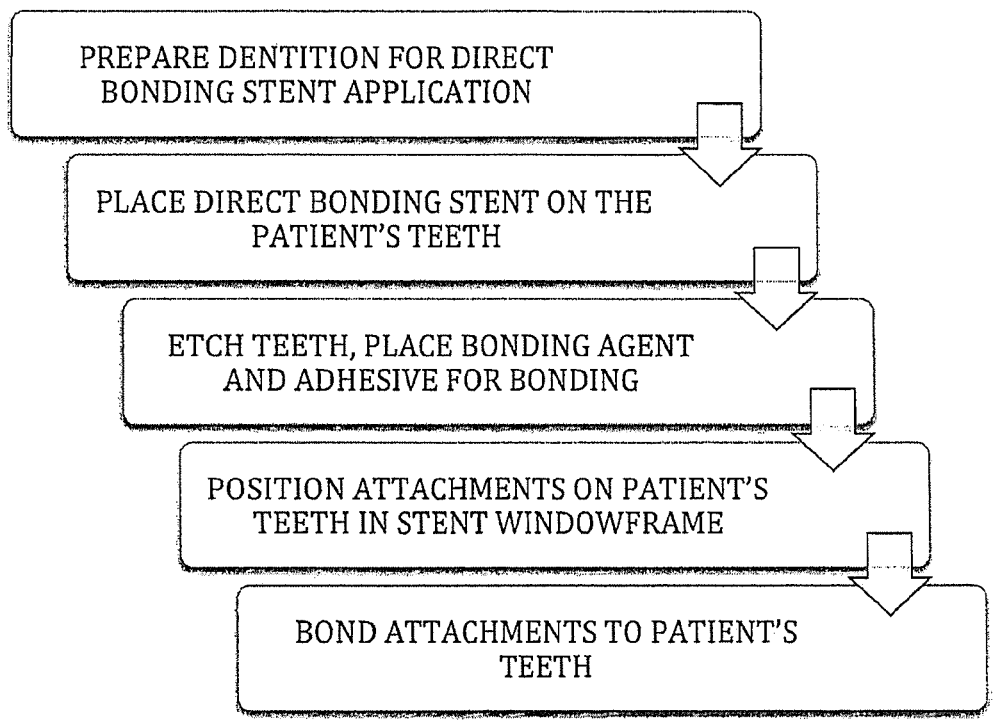
FIG. 5 shows an exemplary method or process for placing an orthodontic attachment on a patient's tooth.

FIG. 5 shows an exemplary method or process for placing orthodontic attachments on a patient's teeth. The process utilizes the direct bonding stent fabricated in the process of FIG. 4A or 4B. To facilitate bonding, the tooth surface is prepared (etched), and a bonding agent is placed (with or without the stent seated). Adhesive is then placed on the base of each attachment, which in turn is then placed on the selected tooth surface (facial or lingual). Following initial seating, any excess adhesive (if not flash free) is removed by the operator. Once the attachment is determined to have been seated satisfactory, the adhesive is cured (bonding the attachment to the tooth). The adhesive may be light or chemical curing. Light curable adhesives employ a photoinitiator that initiates the curing reaction upon exposure to light. Conversely, chemical curing adhesives utilize two or more components that when mixed together initiate curing reaction.

Figure 9A:
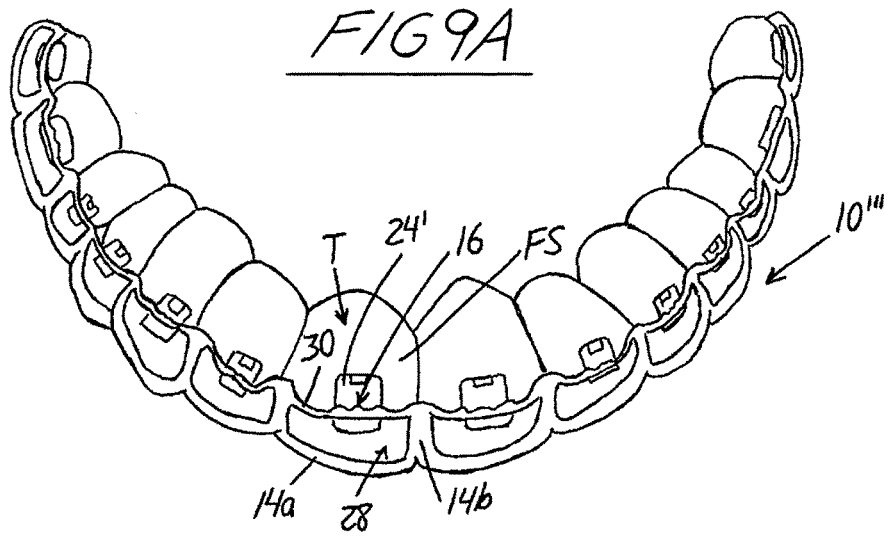
FIG. 9A shows a frontal view of an Intra-arch (Facial) direct bonding stent designed for placement of attachments on the facial surface of teeth in which the incisal support wall portion of the stent window frame is reduced to a facially elevated bridge.
Figure 9B:
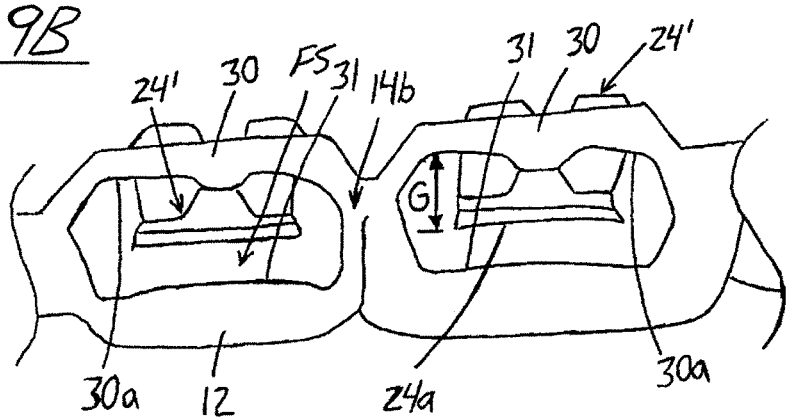
FIG. 9B shows a close-up incisal view of an Intra-ach direct bonding stent in which the incisal support wall portion of the stent window frame is reduced to a facially elevated bridge for improved incisal access during placement of attachments therein.
Figure 9C:
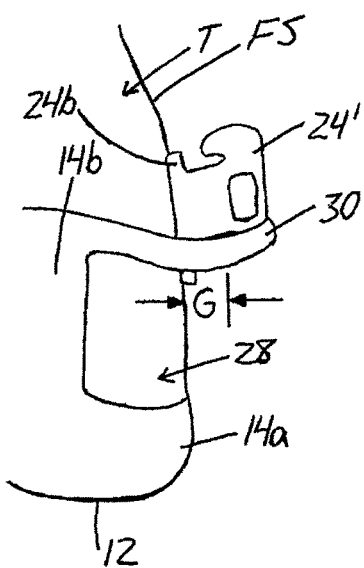
FIG. 9C shows a close-up lateral view of an Intra-ach direct bonding stent in which the incisal support wall portion of the stent window frame is reduced a facially elevated bridge.

FIGS. 9A-9C show another embodiment of a direct bonding stent 10". Whereas the stents of the earlier embodiments have the attachment support wall fully intact over the entire incisal portion of the attachment, i.e. spanning continuously from the occlusal arch-shaped portion 12 to the terminal edge of the support wall 14 over the full-length of the arch, this embodiment instead features a respective void 28 in the support wall 14 at each tooth.

With reference to FIG. 9A, each void 28 is located intermediately between the originating end of the support wall 14 that joins to the occlusal arch-shaped portion 12 and the terminal end of the support wall at which the respective attachment-receiving window is defined. An occlusal/incisal portion 14a of the support wall 14 remains intact at the originating end thereof to connect the support wall to the arch-shaped portion 12, and defines an occlusal/incisal side of the void. Across the void 28 from the occlusal/incisal portion 14a of the support wall 14, the opposing gingival side of the void is defined by a bridge portion 30 of the support wall that spans across the void 28. For all teeth except the rearmost molars, the remaining two sides of each void 28 are defined by intact inter-dental areas 14b of the support walls that overlie the areas between adjacent teeth and span fully from the originating end of the support wall to the opposing bridge portions thereof.

On the gingival side of this bridge portion 30 that faces away from the void 28, the respective window 16 is defined for use in guiding the placement of the respective attachment 24' on the facial surface FS of the respective tooth T during use of the stent, as described herein above for the other illustrated embodiments. The gingival side of the bridge portion 30 is thus shaped to define the two opposing sides 16c, 16d of the respective window 16 and the closed end thereof against which the respective attachment 24' is to be placed. Like the windows 16, the voids 28 pass fully through the support wall in the lingual-buccal direction, but unlike the open-ended windows 16, the voids 28 are closed on all sides thereof.

Turning to FIG. 9B, the tooth-facing lingual side 30a of the bridge portion 30 of the support wall 14 is spaced facially outward from the tooth-facing lingual side 31 of the occlusal/incisal portion 14a of the support wall 14. The distance of this facially outward offsetting of the bridge portion 14a relative to the occlusal/incisal portion 14a exceeds that which is dictated by the curvature of the tooth's facial surface FS, thus resulting in a gap G between the tooth-facing lingual side 30a of the bridge portion 30 of the support wall 14 and the facial surface FS of the tooth when the stent is placed in the worn position. When the respective attachment 24' is seated in the target position against the bridge portion 30, only a facially outer portion of the attachment is directly supported by the narrow bridge portion 30, while an inner lingual portion of the attachment reaches inwardly across the gap G from the bridge portion 30 of the support wall 14 to the facial surface FS of the tooth T. Accordingly, access to the base 24b of the attachment is available via the respective void 28 and the adjoining gap G. The width of the void 28 between the inter-dental areas 14b of the support wall 32, and the corresponding width of the gap G measured in the same direction, both exceed the corresponding width of the respective window 16 and attachment 24', whereby access is available to three of the four sides of the attachment's base 24a through the gap G. This embodiment thus facilitates removal of excess adhesive that may accumulate around the incisal portion of the attachment base, and provides improved visibility to ensure positive seating of attachments on the teeth. As described for other embodiments, the depth of the window at each bridge may be approximately one-third of the attachment height, leaving the gingival two-thirds of the attachment height free of the stent for easy gripping and manipulation thereof, which also helps facilitate passive removal.

While FIG. 9 illustrates a stent whose support wall is on the facial side of the arch-shaped occlusal portion 12 for placement of attachments on the facial surfaces FS of the patient's teeth T, the voids, windows and offset bridge portions could alternatively be used in a lingually positioned support wall for placement of attachments on the lingual surfaces of the teeth. In such instance, the bridge portions will be outwardly offset from the incisal/occlusal portions of the support wall in the lingual, rather than facial direction, likewise creating a gap between the teeth and bridge portions in the lingual-facial direction to enable improved access to the base of the attachment via the respective void. While FIG. 9 shows an intra-arch version of the stent, it will be appreciated that similar use of voids and gaps for improved access and visibility to placed attachments could likewise be employed one or both maxillary and mandibular halves of an inter-arch stent.

While the described embodiments feature a window depth of approximately one-third of the attachment height, the ratio between the window and attachment sizes may be varied while still retaining the advantage of leaving a gingival portion of the attachment exposed outside the constraints of the stent. The illustrated embodiments with a 1:3 ratio of window depth to attachment height is one example of preferred embodiments in which the window depth is 50% or less of the attachment height, while the window depth other embodiments may vary inside or outside the preferred range, for example with window depths between 25% and 50% of the attachment height, between 25% and 60% of the attachment height, or between 25% and 75% of the attachment height. Any stents disclosed herein configured for placement on the maxillary arch may incorporate palatal coverage/extension to increase retention of the stent intraorally.

Since various modifications can be made in my invention as herein above described, and many apparently widely different embodiments of same made within the scope of the claims without departure from such scope, it is intended that all matter contained in the accompanying specification shall be interpreted as illustrative only and not in a limiting sense.

The invention claimed is:

1. A stent for guiding placement of attachments on a patient's teeth, the stent comprising:
   an occlusal arch-shaped portion for fitting against occlusal surfaces of the patient's teeth; and
   an attachment support wall extending in a gingival direction from the occlusal arc-shaped portion along one side thereof; and
   a plurality of voids in said attachment support wall, each void passing through said attachment support wall in a facial-lingual direction;
   a respective bridge portion of the attachment support wall spanning across each void at a gingival side thereof opposite the occlusal arch-shaped portion for seating of a respective attachment against said bridge portion;
   wherein a tooth-facing side of each respective bridge portion is spaced outwardly from a tooth-facing side of an occlusal portion of the attachment support wall that lies across said void from the respective bridge portion and joins with the occlusal arch-shaped portion, whereby during use of the stent on the patient's teeth, each bridge portion is spaced outward from a respective tooth against which the tooth-facing side of the respective arch-shaped portion of the attachment support wall is abutted to create a gap between said bridge portion and said respective tooth by which improved access to the attachment is available for subsequent adhesive removal.

2. The stent of claim 1 comprising a respective window at each bridge portion for placement of the respective attachment into abutment with the respective tooth through said respective window, each window passing through said attachment support wall in the facial-lingual direction and having an open end and an opposing closed end that lies opposite to said open end at said bridge portion, wherein a depth of each window is less than a height of the respective attachment such that the bridge portion of the attachment support wall of the stent stops short of an end of the attachment when the respective attachment is seated against the closed end of the window at said bridge portion.

3. The stent of claim 2 wherein the attachment support wall further comprises bypass openings therein that pass fully therethrough in the facial-lingual direction and that open into the support wall from opposite the occlusal arch-shaped portion, each bypass opening being larger than the windows so as to space the stent away from existing attachments on the patient's teeth at the bypass openings during repositioning of other existing attachments on the patient's teeth via the windows.

4. The stent of claim 2 wherein a posterior window located posteriorly of at least one other window is deeper at a distal side of said posteriorly located window than at an opposing mesial side thereof to improve access to posteriorly located window from the mesial side.

5. The stent of claim 2 wherein the support wall comprises at least one inter-dental area of reduced lingual-facial thickness that is located between a respective pair of first and second windows, of which the second window is located posteriorly of the first window, and the inter-dental area of reduced lingual-facial thickness slopes distally and gingivally toward the second window for improved mesial access to said second window.

6. The stent of claim 2 comprising contrasting coloration or distinctive markings at or adjacent boundaries of the windows.

7. The stent of claim 2 wherein a contact surface of the attachment support wall that is positioned for placement against the patient's teeth consists of semi-rigid material of elastomeric properties so as to provide an intimate-cohesive seal between said attachment support wall and the patient's teeth.

8. The stent of claim 1 wherein the attachment support wall extends gingivally from the occlusal arch-shaped portion in two opposing directions, and comprises a first set of said voids and respective bridge portions situated superiorly of the occlusal arch-shaped portion for placement of respective attachments on the patient's maxillary teeth and a second set of voids and respective bridge portions situated inferiorly of the occlusal arch-shaped portion for placement of respective attachments on the patient's mandibular teeth.

9. The stent of claim 8 wherein the occlusal arch-shaped portion comprises at least one passage extending therethrough in the facial-lingual direction.

10. The stent of claim 9 wherein the at least one passage includes a suction passage situated centrally of the occlusal arch-shaped portion at an anterior apex thereof and equipped with a connection at a facial end of said passage for coupling of a vacuum source thereto.

11. The stent of claim 8 wherein the occlusal arch-shaped portion comprises a material of greater rigidity than the attachment support wall.

12. The stent of claim 11 wherein the occlusal arch-shaped portion comprises upper and lower layers for respective contact with the patient's maxillary and mandibular teeth and an intermediate layer disposed between said upper and lower layers, and the intermediate layer is materially distinct from the upper and lower layers and comprises the material of greater rigidity.

13. The stent of claim 1 comprising a second wall extending in the gingival direction from the occlusal arc-shaped portion along a second side thereof opposite to the attachment supporting wall, wherein the second wall is of lesser height than the attachment supporting wall in the gingival direction.

14. The stent of claim 13 wherein the second wall is shaped to terminate short of a curvature cresting point of each tooth in a facial-lingual plane thereof.

15. The stent of claim 1 wherein the attachment support wall extends from the occlusal arch-shaped portion at a lingual side thereof.

16. The stent of claim 1 wherein each void is of greater width than the respective attachment.

17. A method of placing one or more attachments on a patient's teeth, the method comprising:
   obtaining a stent having:
     an occlusal arch-shaped portion for fitting against occlusal surfaces of the patient's teeth;
     an attachment support wall extending in a gingival direction from the occlusal arc-shaped portion along one side thereof; and
     a plurality of voids in said attachment support wall, each void passing through said attachment support wall in a facial-lingual direction; and
     a respective bridge portion of the attachment support wall spanning across each void for seating of a respective attachment against said bridge portion;
   positioning the stent on the patient's teeth, including placing each bridge portion at a location spaced outward from a respective tooth to leave a gap between said bridge portion and said respective tooth;
   placing a base of a selected attachment against the respective tooth in a position seating the attachment against the respective bridge portion at said location spaced outwardly from the respective tooth, from which the attachment reaches inward to the respective tooth across said gap, whereby said gap provides improved access to the attachment for subsequent adhesive removal.

18. The method of claim 17 further comprising adhesively bonding the selected attachment to the tooth in said target position, and removing excess adhesive from around the base of the attachment via the respective void.

\* \* \* \* \*